(12) United States Patent
Parker et al.

(10) Patent No.: US 6,321,113 B1
(45) Date of Patent: Nov. 20, 2001

(54) AUTOMATIC EXTERNAL DEFIBRILLATOR FIRST RESPONDER AND CLINICAL DATA OUTCOME MANAGEMENT SYSTEM

(75) Inventors: William S. Parker, Maple Grove; Patrick J. Splinter; Sarah M. Lindseth, both of Eden Prairie; Matthew G. Bradley, Mankato, all of MN (US)

(73) Assignee: SurVivaLink Corporation, Minneapolis, MN (US)

( * ) Notice: Subject to any disclaimer, the term of this patent is extended or adjusted under 35 U.S.C. 154(b) by 0 days.

(21) Appl. No.: 09/281,076

(22) Filed: Mar. 30, 1999

Related U.S. Application Data

(60) Provisional application No. 60/080,130, filed on Mar. 31, 1998.

(51) Int. Cl.⁷ ........................................................ A61N 1/39
(52) U.S. Cl. .................................................................. 607/5
(58) Field of Search ........................ 607/5, 300; 600/523; 128/903, 920

(56) References Cited

U.S. PATENT DOCUMENTS

| | | |
|---|---|---|
| 3,925,762 | 12/1975 | Heitlinger et al. . |
| 4,216,462 | 8/1980 | McGrath et al. . |
| 4,281,330 | 7/1981 | Warrick . |
| 4,290,114 * | 9/1981 | Sinay .................................. 128/920 |
| 4,319,241 * | 3/1982 | Mount ................................ 128/903 |
| 4,715,385 | 12/1987 | Cudahy et al. . |
| 4,895,161 | 1/1990 | Cudahy et al. . |
| 5,243,975 | 9/1993 | Alferness et al. . |
| 5,345,552 | 9/1994 | Brown . |
| 5,456,261 | 10/1995 | Luczyk . |
| 5,549,115 | 8/1996 | Morgan et al. . |
| 5,549,659 | 8/1996 | Johansen et al. . |
| 5,593,426 | 1/1997 | Morgan et al. . |
| 5,680,864 | 10/1997 | Morgan et al. . |
| 5,716,380 | 2/1998 | Yerkovich et al. . |

FOREIGN PATENT DOCUMENTS

WO 96/14620    5/1996   (WO) .

\* cited by examiner

Primary Examiner—William E. Kamm
(74) Attorney, Agent, or Firm—Patterson, Thuente, Skaar & Christensen, P.A.

(57) ABSTRACT

A method and system for managing cardiac rescue events is disclosed. Unlike prior systems, this method and system uses a rescue scene computer to obtain patient and incident data at the rescue scene and then marry that data with ECG rescue data and automated external defibrillator (AED) rescue data. All of this data is then simultaneously transmitted to a base computer at an emergency medical center for review. Accordingly, a reviewer at the base computer can immediately review the ECG and AED performance in context with patient and incident data. The method and system includes a Windows-based single screen graphical user interface for entering and reviewing the data and particularly includes a window for viewing ECG data simultaneously with entry and review of all other data available in the single screen user interface. The system and method comprises one or more of the following elements including a base computer, a portable rescue scene computer, an automated external defibrillator (AED), and a communication link for linking the rescue scene computer to the base computer and/or the AED. The system and method further includes software that is programmed in the base computer and rescue scene computer to operate the single screen user interface and database.

16 Claims, 17 Drawing Sheets

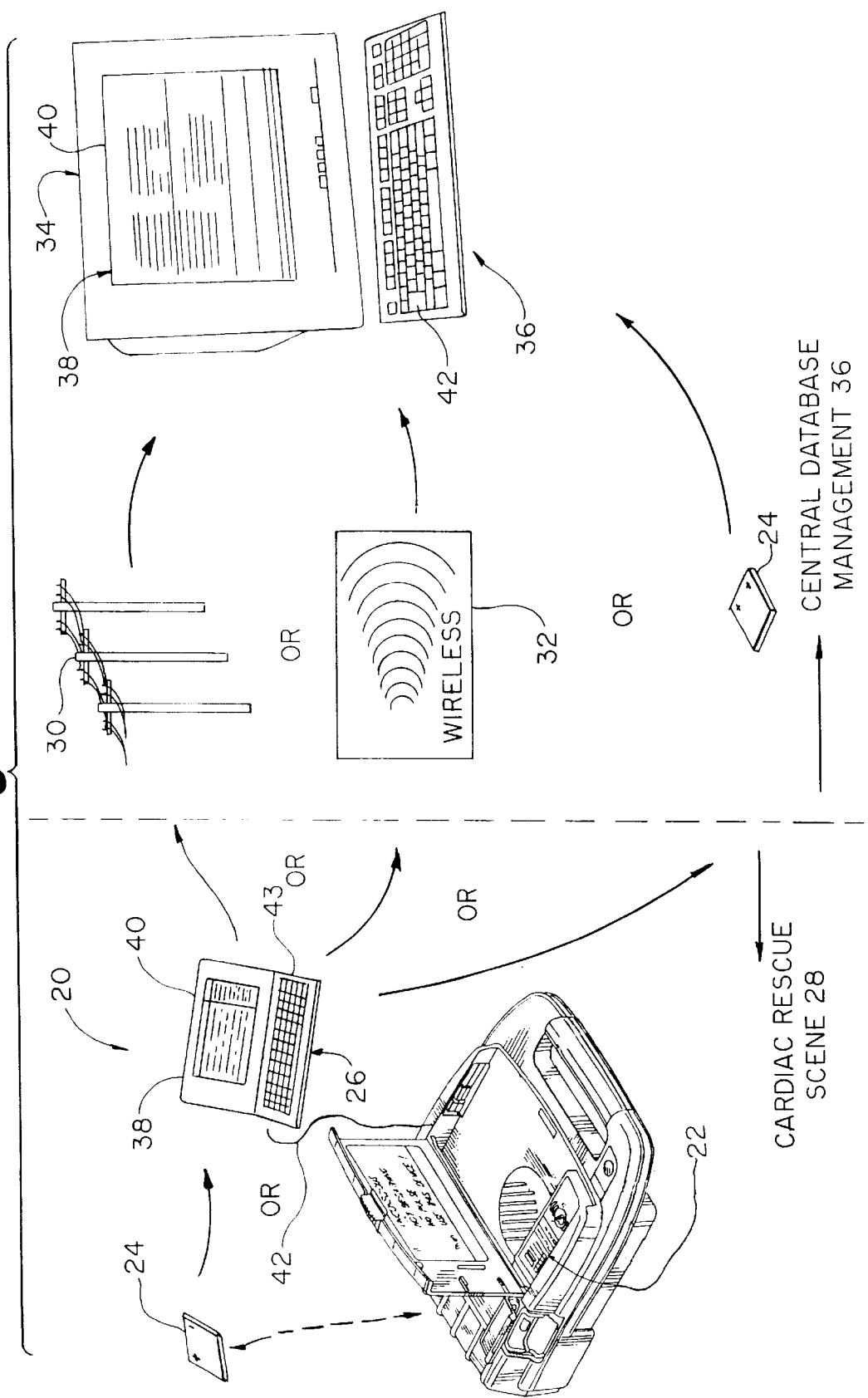

(Figure showing software screen "DATA STORM - [NOT INTENDED FOR TREATMENT OR DIAGNOSIS OF PATIENT]" with menus: INCIDENT TOOLS COMMUNICATIONS RECORD VIEW PLAYBACK HELP. Fields include INCIDENT ID: PITTSBUR, INCIDENT DATE: 6/26/97, INCIDENT TIME: 9:02:43 AM, INCIDENT TYPE: EDUCATIONAL INSTITUTION with dropdown list showing: "EDIT LIST", EDUCATIONAL INSTITUTION, FARM, HOME/RESIDENCE, INDUST. PLACE AND PREM., MINE OR QUARY, OTHER SPEC. LOCATION, PLACE FOR REC OR SPORT, PUBLIC BUILDING, RESIDENTIAL INSTITUTION. Also SERVICE AREA, PATIENT INFO, PATIENT ID, PATIENT FIRST, MIDDLE, LAST, PATIENT DESCRIPTION, DATE OF BIRTH, AGE AT TIME OF INCIDENT. Right side shows ADDRESS, CITY, STATE: MINNESOTA, ZIP CODE, COUNTRY, COUNTY, GEO CODE, tabs ERAPY DISPATCH SUMMARY AED DATA REVIEW AED EVALUATION NOTES, SSN/ID, PATIENT ADDRESS with ADDRESS, CITY, STATE, ZIP CODE, COUNTY. Timeline at bottom 00:00:00 to 00:00:08 with LID OPEN marker. Labels: 52, 86, 87B, 87A, 50. "FOR HELP PRESS F1")

Fig. 2C

(Dialog box "ADD/EDIT ITEM" with INCIDENT TYPE: EDUCATIONAL INSTITUTION, CODE: 849.7, OK and CANCEL buttons. Labels: 87C, 87D, 86, 87E)

Fig. 3

DATA STORM - [NOT INTENDED FOR TREATMENT OR DIAGNOSIS OF PATIENT]
INCIDENT TOOLS COMMUNICATIONS RECORD VIEW PLAYBACK HELP

INCIDENT INFORMATION
RESCUE SCENE
ASSESSMENT

| Field | Value |
|---|---|
| INCIDENT ID | 071298 |
| INCIDENT DATE | 6/26/1998 |
| INCIDENT TIME | 8:55:43 AM |
| INCIDENT TYPE | HOME/RESIDENCE |
| SERVICE AREA | MAPLE GROVE |
| ADDRESS | 8051 ORCHID LANE |
| CITY | MAPLE GROVE |
| ZIP CODE | 55311-2117 |
| COUNTY | HENNEPIN |

PATIENT INFORMATION | INCIDENT DATA | VITALS AND THERAPY | DISPATCH SUMMARY | AED DATA | REVIEW | AED EVALUATION | NOTES

| Field | Value |
|---|---|
| CHIEF COMPLAINT | CHEST PAIN |
| CAUSE OF INJURY | MOTOR VEHICLE TRAFFIC ACCIDENT |
| PROVIDER IMPRESSION | CARDIAC ARREST |
| PRE-EXISTING CONDITION | NONE |
| SIGNS AND SYMPTOMS PRESENT | CHEST PAIN |
| INJURY DESCRIPTION | |
| INJURY INTENT | INTENTION, OTHER |
| INCIDENT/PATIENT DISPOSITION | TREATED AND TRANSPORTED BY EMS |
| SAFETY EQUIPMENT | HELMET USED |
| FACTORS AFFECTING EMS DELIVERY | NOT APPLICABLE |
| SUSPECTED ALCOHOL/DRUG ABUSE | NO |

FOR HELP, PRESS F1

AUTOMATIC EXTERNAL DEFIBRILLATOR FIRST RESPONDER AND CLINICAL DATA OUTCOME MANAGEMENT SYSTEM

RELATED APPLICATION

This application claims the benefit of U.S. Provisional Application No. 60/080,130, filed Mar. 31, 1998, incorporated herein in its entirety by reference.

FIELD OF THE INVENTION

The present invention relates to medical emergency event management and, in particular, relates to a computer-based communications network and database for management of emergency medical events such as sudden cardiac arrest rescue events.

BACKGROUND OF THE INVENTION

Cardiac arrest, exposure to high-voltage power lines, and other trauma to the body can result in ventricular fibrillation which is the rapid and uncoordinated contraction of the myocardium. The use of external defibrillators to restore the heartbeat to its normal pace through the application of electrical shock is a well-recognized and important tool in resuscitating patients. External defibrillation is used in emergency settings in which the patient is either unconscious or otherwise unable to communicate.

Automated external defibrillators (AEDs) are used by first responders such as police officers, paramedics, and other emergency medical technicians to resuscitate cardiac arrest patients. The AED must be used quickly and properly by the first responder, since the chance of successfully resuscitating the patient decreases approximately 10 percent-per-minute following cardiac arrest.

With the advent of emerging technologies such as AEDs, emergency medical systems (EMS) have greater opportunities for saving lives. However, because of increasing health care costs, an elevated standard of care, and competitiveness in the health care provider market, EMS directors must improve their management of cardiac rescue events with AEDs.

Unfortunately, current attempts at managing performance of sudden cardiac arrest rescues suffer from a lack of coordination and cohesiveness that is necessary to accurately and comprehensively track and evaluate out-of-hospital cardiac arrest rescues. For example, data regarding a cardiac rescue attempt typically arrives to the EMS director from several sources, occurring at different points in time, and commonly in different formats which must be integrated away from the cardiac rescue site. Moreover, current techniques of reviewing cardiac rescue events lack the appropriate data to make significant strides in improving the quality of out-of-hospital cardiac arrests. Finally, conventional computer-based tools for integrating and reviewing cardiac rescue data inflexibly require separate review and analysis of the incident, the AED and AED operator performance, and the ECG.

SUMMARY OF THE INVENTION

A method and system of the present invention manages cardiac rescue events. Unlike prior systems, this method and system uses a rescue scene computer to obtain patient and incident data at the rescue scene and then marry that data with ECG rescue data and automated external defibrillator (AED) rescue data. All of these data are then simultaneously transmitted to a base computer at an emergency medical center for review. Accordingly, a reviewer at the base computer can immediately review the ECG and AED performance in context with patient and incident data.

The method and system includes a Windows®-based single screen graphical user interface for entering and reviewing the data, and particularly includes a window for viewing ECG data simultaneously with entry and review of all other data available in the single screen user interface.

In addition, as data (e.g., ECG, patient, incident, AED, etc.) are placed in the system, these data are instantly registered by the system with corresponding NHSTA codes. This feature automatically readies the cardiac rescue data for reporting to national authorities. In addition, the NHSTA codes are embedded in the background of the active data fields to permit selective activation, deactivation, modification, and/or initialization. Moreover, appropriate data fields are supplied to insure all data for UTSTEIN-style reporting is obtained to permit UTSTEIN-style reporting of out-of-hospital cardiac arrest.

Finally, the system and method uses open database connectivity (ODBC) to permit any desired data from a cardiac rescue event that are logged into other types of systems and methods to be imported into the method and system of the present invention. Similarly, data from the system and method of the present invention can be exported to other ODBC-compatible data management systems and methods for further review, revision, or publication.

The system and method comprises one or more of the following elements including a base computer, a portable rescue scene computer, an automated external defibrillator (AED), and a communication link for linking the rescue scene computer to the base computer and/or the AED. The system and method further includes software that is programmed in the base computer and rescue scene computer to operate the single screen user interface and database.

BRIEF DESCRIPTION OF THE DRAWINGS

FIG. 1 is a schematic illustration of a cardiac rescue event data management system and method of the present invention.

FIG. 2A is a schematic representation of a rescue scene location screen and patient information tab window, with optional simultaneous ECG display, of a graphical user interface of the system and method of the present invention.

FIG. 2B is a schematic representation of a drop-down table for an incident type data field of the rescue scene location view screen of FIG. 2A.

FIG. 2C is a schematic representation of an edit window for the drop-down table of FIG. 2B showing a NHSTA code corresponding to the incident type data field entry.

FIG. 3 is a schematic representation of an incident information tab window, with optional simultaneous ECG display, of a graphical user interface of the system and method of the present invention.

FIG. 4 is a schematic representation of a patient vitals and therapy information tab window, with optional simultaneous ECG display, of a graphical user interface of the system and method of the present invention.

Figure 5A:
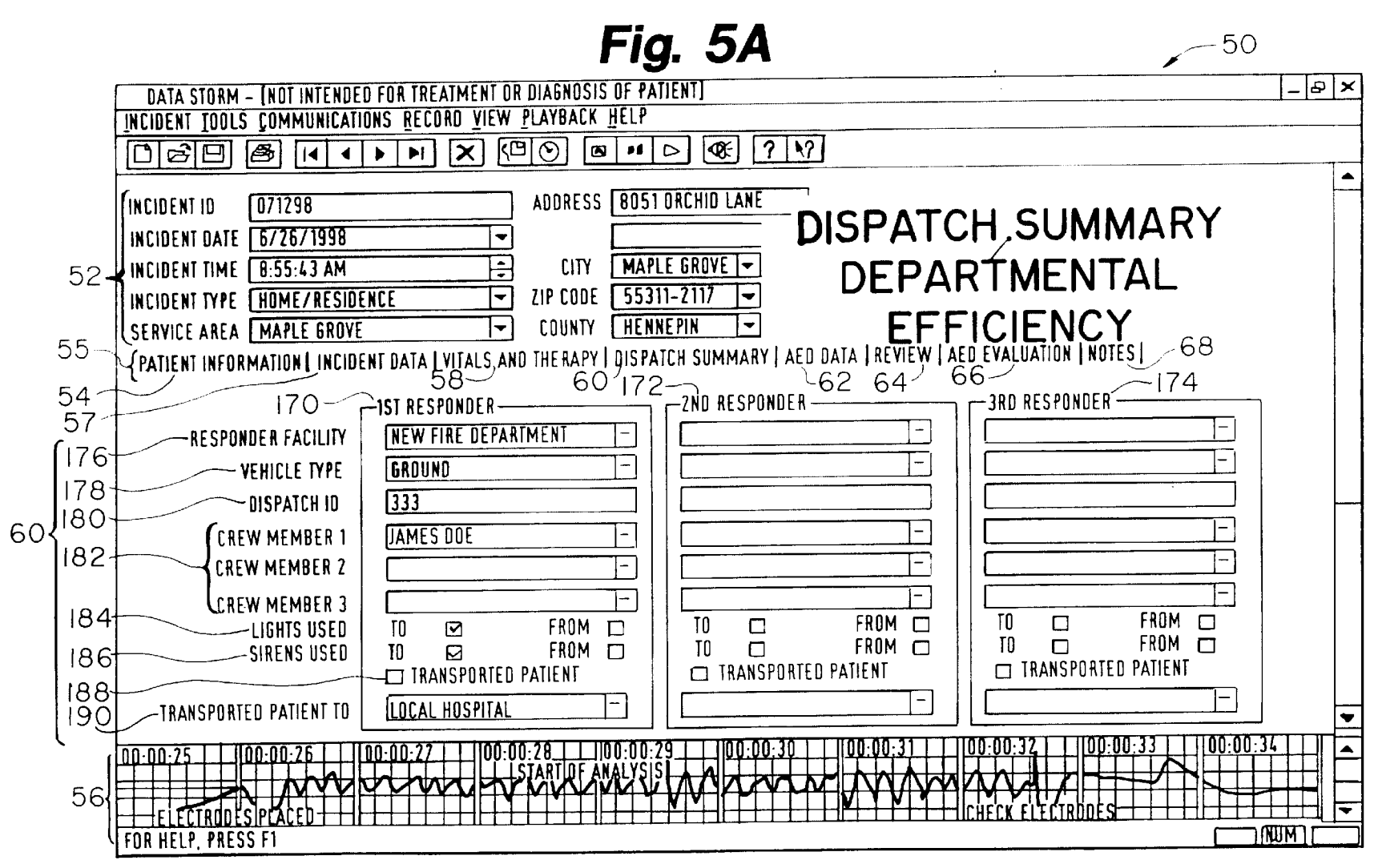

FIGS. 5A–5B are schematic representations of a rescue dispatch information tab window, with optional simultaneous ECG display, of a graphical user interface of the system and method of the present invention.

FIGS. 6A–6B are schematic representations of an automated external defibrillator and operator performance tab window, with optional simultaneous ECG display, of a graphical user interface of the system and method of the present invention.

FIGS. 7A–7B are schematic representations of a patient outcome tab window, with optional simultaneous ECG display, of a graphical user interface of the system and method of the present invention.

FIG. 9 is a schematic representation of a reviewer note tab window, with optional simultaneous ECG display, of a graphical user interface of the system and method of the present invention.

FIG. 11 is a schematic representation of an AED deployment tool window of the method and system of the present invention.

FIG. 12 is a schematic representation of an AED training tool window of the method and system of the present invention.

DETAILED DESCRIPTION OF THE PREFERRED EMBODIMENTS

Figure 5B:
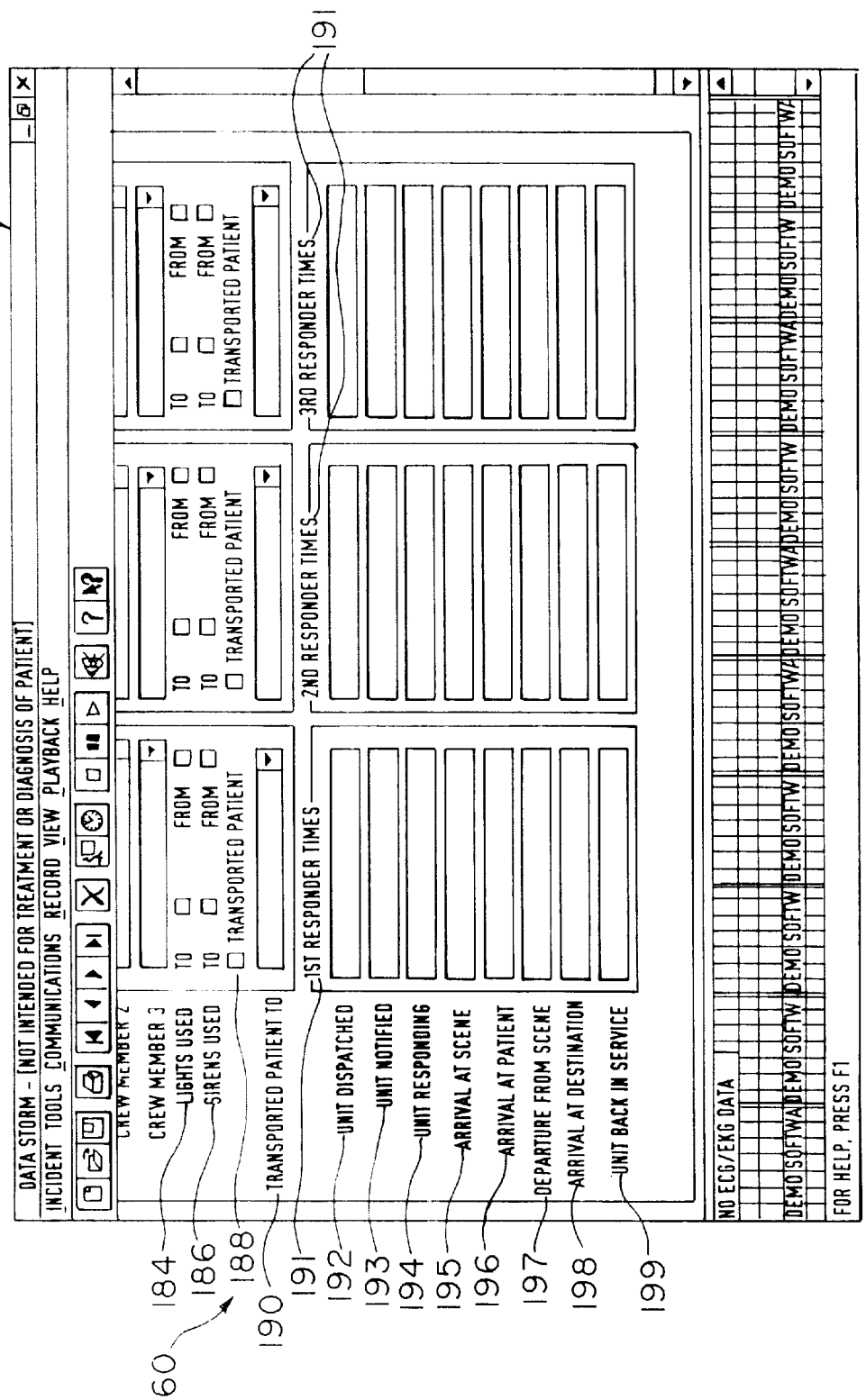

A method and system for managing cardiac rescues of the present invention is schematically shown in FIG. 1 at 20. System 20 includes AED 22, AED data card 24, and rescue scene computer 26, all locatable at cardiac rescue scene 28. System 20 further includes land line communication link 30 or wireless link 32 and base computer 34 at database management or emergency medical center 36.

Both rescue scene computer 26 and base computer 34 further include display 38 with graphical user interface 40 (i.e., view screen) and input means 42 such as a keyboard for entering data into the view screen of the user interface. AED 22 further includes a cable 43 for communicating with rescue scene computer 26.

AED 22 preferably includes an AED such as the one disclosed in Olson, et. al, U.S. Pat. No. 5,645,571, titled AUTOMATED EXTERNAL DEFIBRILLATOR WITH LID ACTIVATED SELF-TEST SYSTEM, which is hereby incorporated by reference in its entirety. AED 22 is capable of recording an ECG on a patient, and advising and delivering an electrical shock as necessary. The AED also makes an audio recording at the cardiac rescue scene of an operator's or bystander's voice during the ECG. Data from the cardiac rescue event, including the ECG recorded in real time, data from AED-detectable events (e.g., check electrodes, place electrodes, rhythm analyzed, shock advised, shock delivered, etc.), and the audio recording are recorded internally within AED 22 for later downloading to a computer for further analysis. The data can also be stored onto a data storage card that is removably insertable into AED 22, such as AED memory data card 24. AED memory data card 24 is, in turn, removably insertable into rescue scene computer 26, or into base computer 34, for transferring the ECG and AED performance data from AED 22 into the respective rescue scene computer 26 or base computer 34. Alternatively, the data can be downloaded from AED 22 into rescue scene computer 26 via cable 43.

Rescue scene computer 26 and base computer 34 are both general purpose personal computers well known in the art. For example, both rescue scene computer 26 and base computer 34 include, at a minimum, a CPU such as a 486SX-66 MHz (or faster) processor. Rescue scene computer 26 and base computer 34 also include sufficient RAM memory (e.g., 16 megabytes) and hard drive memory (e.g., 80 megabytes) to store and operate Microsoft® Windows 95 or NT and the database software (e.g., Microsoft® Access) supporting the system and method of the present invention. Rescue scene computer 26 includes any portable computer such as a laptop personal computer (PC) or a handheld PC.

During a cardiac rescue event, a first responder or other operator uses AED 22 to defibrillate a cardiac arrest patient. Data representing the ECG and the AED/AED operator performance are recorded internally within AED 22 and then transferred onto AED data card 24. Next, this ECG/AED data are transferred into rescue scene computer 26 via cable 43, or by removal of AED data card 24 from AED 22, and into rescue scene computer 26. In addition, while at the rescue scene, the first responder or other technician manually enters patient and incident data regarding the cardiac rescue event into rescue scene computer 26. With all of the ECG data, AED data, and non-ECG data (e.g., patient and incident information) loaded into rescue scene computer 26, this entire set of data is transmitted via landline link 30 or wireless link 32 to base computer 34 at a central emergency medical system center 36.

The ECG data, AED data, and non-ECG data are then observable together in an integrated fashion on base computer 34 in single screen graphical user interface 40. All of this data can be reviewed or modified as necessary, while additional information regarding the cardiac rescue event, including post event care and related emergency medical system performance, can be entered by the user through the single screen user interface 40 using input means 42. Using this technique, data are comprehensively and accurately captured to permit meaningful and rapid evaluation of each cardiac rescue event. Over time, as the system and method of the present invention is applied across localities, states, and nationally, for multiple cardiac rescue events, a tremendous database will be developed. This information will greatly contribute to improving rescue techniques and understanding the delivery and effectiveness of emergency medical intervention.

The remaining description explains single screen user interface 40 in greater detail, including how and where the ECG data, AED data, and non-ECG data are displayed as well as how other cardiac rescue event performance, evaluation, and reporting information is handled.

Figure 2A:
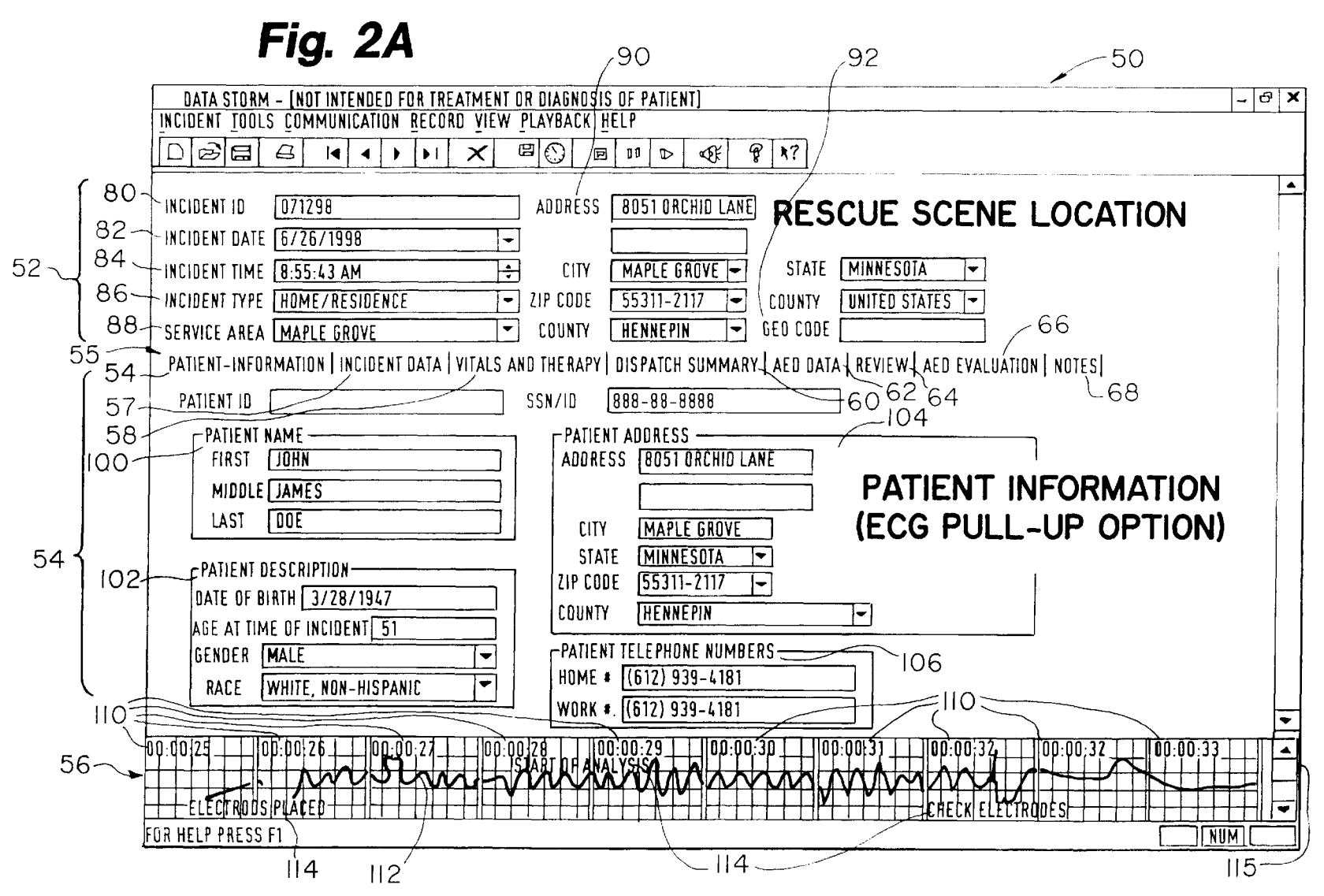

FIG. 2 is a schematic representation of single screen graphical user interface 40 permitting entry, review, and revision of data regarding a cardiac rescue event. Interface 40 defines single view screen 50 having resident components, such as rescue scene location 52, and selective viewing components, such as patient information tab window 54, and optional ECG window 56. Tabs 55 mark access to selectable patient information tab window 54 as well as other selectable tab windows such as incident data window 57, vitals and therapy window 58, dispatch summary window 60, AED data window 62, review window 64, AED evaluation window 66, and notes window 68. Once a tab is selected, the window corresponding to that tab is displayed in an overlay fashion over the other tab windows. Data is entered via input means 42 into the data fields visible in the selected window, which correspond directly with data fields of the database that operates in the background (not visible). Data fields within the tab windows include stored data in drop-down windows that can be selected and/or are capable of receiving manually entered new data.

At the rescue scene, an operator fills in the data fields of rescue scene location screen 52 using input means 42 of rescue scene computer 26 to collect general information about the patient and the incident. As shown in FIG. 2, rescue scene location screen 52 includes the following data fields: incident ID 80, incident date 82, incident time 84, incident type 86, service area 88, rescue address 90 (street, city, state, zip code, country, county), and geographic code 92. Rescue scene location screen 52 always remains active in single screen user interface 40. Patient information tab window 54 includes the following data fields: patient name 100, patient description 102 (such as date of birth, age, gender, race), patient address 104 (street, city, state, zip code, county), and patient telephone 106.

FIG. 2 also shows ECG pull-up window 56 which graphically displays a real time representation of the ECG recorded during the cardiac rescue event with AED 22. ECG pull-up window 56 includes the following data fields: real time stamp 110, ECG waveform 112, and AED event stamp 114 (e.g., electrodes placed, start of analysis, check electrodes). ECG window 56 defines a splitter window 115 that can be reduced or enlarged vertically on single screen user interface 40. ECG window 56 also can be deactivated for selective removal from single screen user interface 40. All of the textual and graphically represented data in the ECG window 56 is obtained from AED 22.

When deployed in a handheld PC embodiment, rescue scene computer 26 operates a simpler graphical user interface like single screen user interface 40 that includes at least the corresponding data fields from patient information tab window 54 and incident information tab window 57 (described below).

The database supporting single screen graphical user interface 40 was constructed using Windows® operating system and Access® database system, both sold by Microsoft Corporation. Accordingly, the multiple tab window structure within the single screen user interface 40, as well as the optional simultaneous ECG window 56, can be constructed by one skilled in the art using the tools and capabilities of Access® database program and Windows® operating system. In particular, the data access object (DAO) mode of the Access® program can be used to identify the desired data fields and relationship tables of the database, as well as the NHSTA codes further described below. The system and method of the present invention also includes an embedded registry of certain National Highway Safety Traffic Administration (NHSTA) codes that is linked to corresponding cardiac/accident rescue data fields. The NHSTA codes used in the method and system of the present invention are published in Federal Information Standard (FIPS) Publication 28, and in International Classification of Disease and Related Health Problems Ninth Revision (ICD-9) and the Tenth Revision (ICD-10). The database is built in the open database connectivity format (ODBC) to permit data to be imported and exported entirely, or selectively, using an ODBC data management program such as Access®, FoxPro®, or SQL®, all known to those skilled in the art. For example, a common ODBC program can be used to extract all or some of the NHSTA-related data from the system. To do so, the user identifies the tables and data fields carrying an embedded NHSTA code (or other desired category of information) and marks them for extraction. Once all of the NHSTA-related data are exported, it can be further manipulated by the ODBC program into a format suitable for reporting to national, state or local authorities. Similarly, data can be extracted for other reporting purposes such as UTSTEIN-style reporting to national, state or local authorities, or for billing purposes with additional modification of the database of the method and the system of the present invention.

The corresponding NHSTA codes for a given data field can be modified, added, or deleted by operating an edit list for the data field and then entering or editing the NHSTA code designation corresponding to that data field. For example, as shown in FIG. 2B, drop-down table 87A for the data field incident type 86 of rescue scene location 52 is selected, displaying several choices to fill this data field as well as "edit list" function 87B. By selecting the "edit list" function, another edit window, shown in FIG. 2C, is ultimately displayed on single screen user interface 40, which displays the data field, its entry, and the corresponding NHSTA code 87E for that entry. The default NHSTA code is displayed, if available, which can be modified, deleted, or added as necessary.

FIG. 3 shows single screen user interface 40 with incident data tab window 57 selected and optional ECG window 56 activated. Like patient tab window 54, incident tab window 57 is used at the cardiac rescue scene to prompt the user to collect information about the incident, which will be transmitted to base computer 34 with patient data, ECG data, and AED data. Incident data tab window 56 includes the following data fields: chief complaint 120, cause of injury 122, provider impression 124, pre-existing condition 126, signs and symptoms present 128, injury description 130, injury intent 132, incident/patient disposition 134, safety equipment 136, factors affecting EMS delivery 138, suspected alcohol/drug abuse 140.

Figure 4:
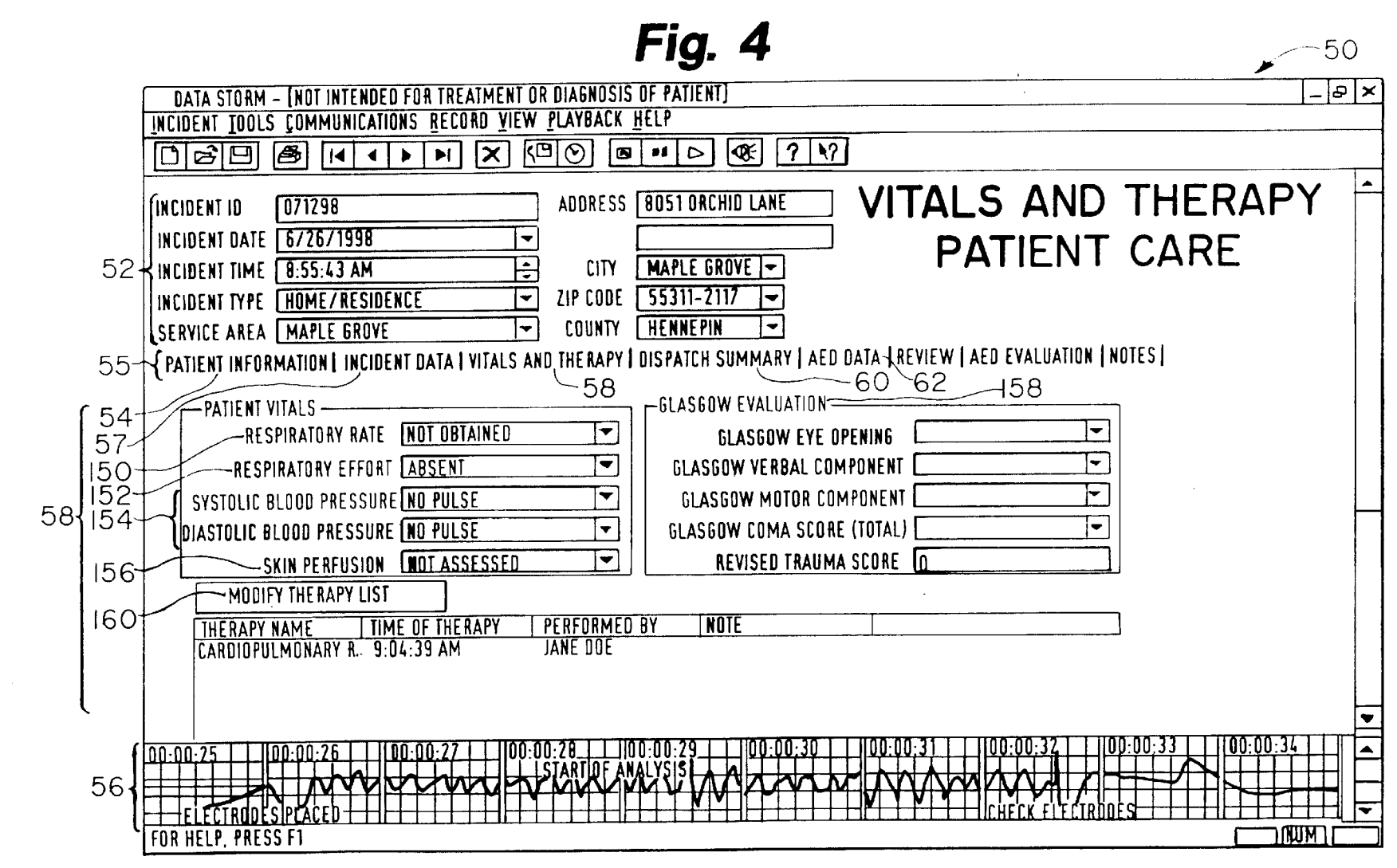

FIG. 4 shows single screen user interface 40 with vitals and therapy tab window 58. The patient vitals and therapy data are typically collected at the cardiac rescue scene with the other patient data (tab window 54) and included for transmission with the ECG data to base computer 34. Once the vitals and therapy tab is selected, window 58 displays and includes the following data fields: respiratory rate 150, respiratory effort 152, blood pressure 154, skin perfusion 156, with Glasgow evaluation 158 (including eye opening, verbal component, motor component, coma score, and revised trauma score), modified therapy list 160 (including therapy name, therapy time, therapy performer, and notes).

FIG. 5A shows single screen user interface 40 with dispatch summary tab window 60 selected, and which includes the following data fields for first responder 170, second responder 172, and third responder 174: responder facility 176, vehicle type 178, dispatch ID 180, crew members 182, lights used 184, sirens used 186, transported patient 188, and location to which patient was transported 190. As shown in FIG. 5B, a lower portion of dispatch summary tab window 60 includes additional data fields for each of first, second and third responder times 191 comprising: unit dispatched 192, unit notified 193, unit responding 194, arrival at scene 195, arrival at patient 196, dispatched from scene 197, arrival at destination 198, and unit back in service 199. The data in the dispatch summary tab window can be entered into the system by rescue personnel either at the cardiac rescue scene and during continuing emergency medical service (e.g., transport to a hospital), or can be entered into the single screen user interface at base computer 34 at a later time with information obtained from the rescue dispatch team after the rescue team reports its activities back to the rescue dispatch center.

Figure 6A:
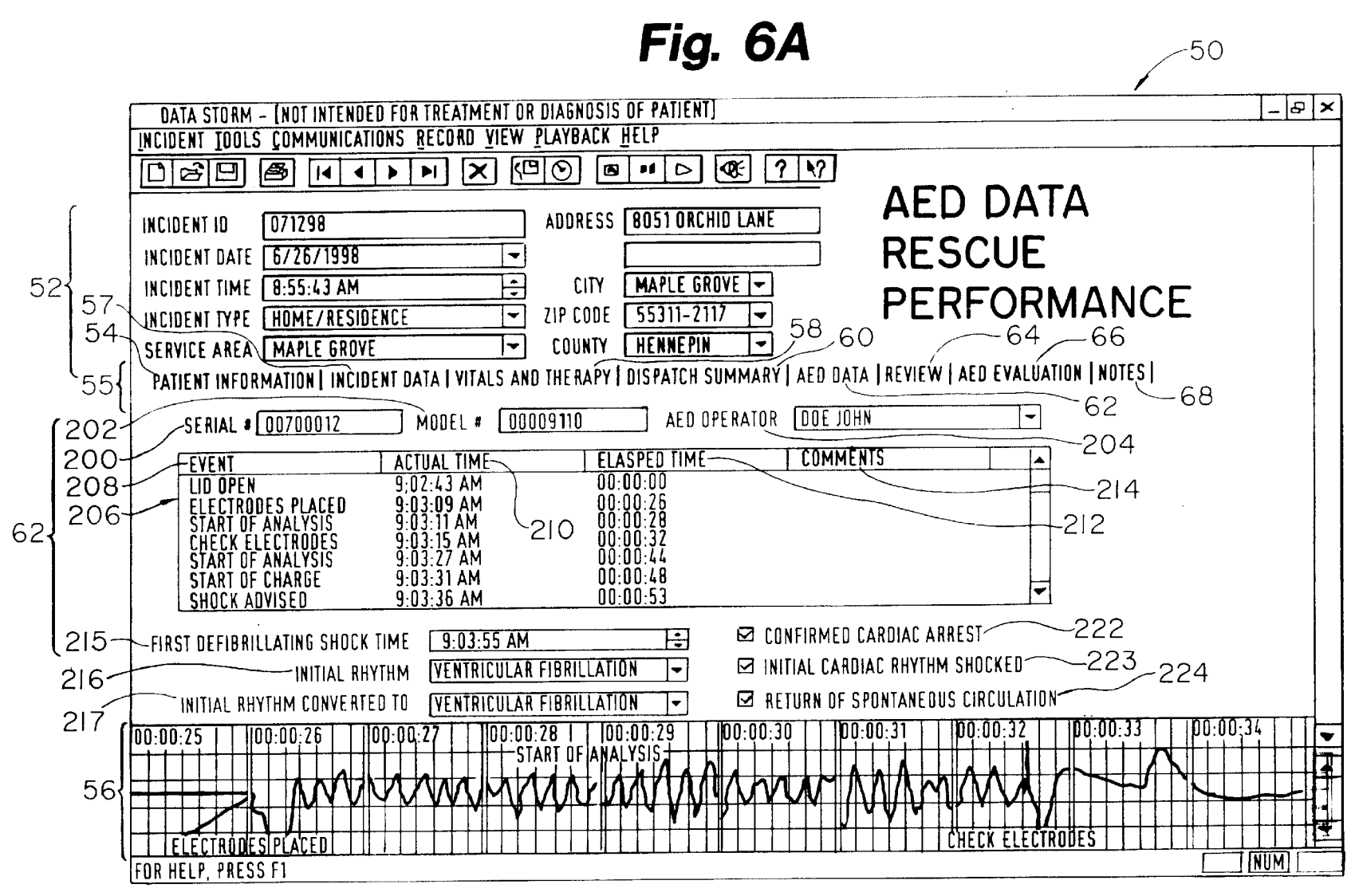
Figure 6B:
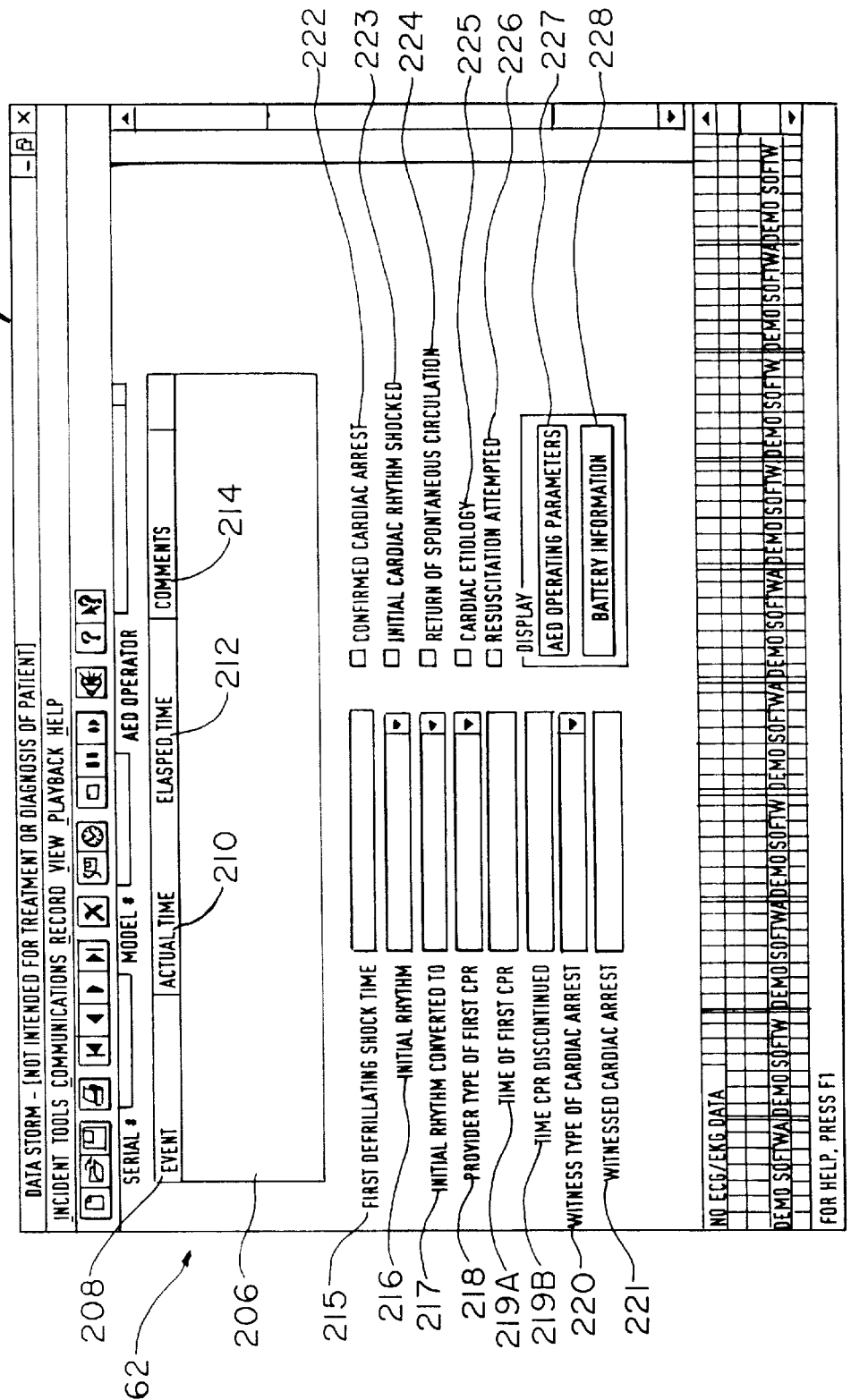

FIGS. 6A–6B show single screen user interface 40 with AED data tab window 62 selected, which includes the following data fields: AED serial number 200, model number 202, AED operator 204, and AED history 206 including event 208 (AED lid opened, electrodes placed . . . , shock advised), actual time 210 (i.e., real time), elapsed time 212, and comments 214 as well as first defibrillating shock time 215, initial rhythm 216 (e.g., ventricular fibrillation), initial rhythm converted to rhythm 217 (e.g., ventricular fibrillation). Additional data fields in AED data tab window 62 primarily relate to UTSTEIN-style reporting of out-of-hospital cardiac arrests, and include: provider type of first CPR 218, time of first CPR 219A, time CPR discontinued 219B, witness type of cardiac arrest 220, witnessed cardiac arrest 221, confirmed cardiac arrest 222, initial cardiac rhythm shocked 223, and return of spontaneous circulation (ROSC) 224, cardiac etiology 225, resuscitation attempted 226. Finally, tab window 62 includes display AED operating parameters look-up window 227, and battery information look-up window 228. Most of the AED- and ECG-related data fields in AED data tab window 62 is automatically entered into the method and system of the present invention when this data is downloaded from AED 22 into rescue scene computer 26 and/or base computer 34. Of course, those data fields not filled in by data from AED 22 are filled in manually by an operator at the rescue scene or at a later time by a reviewer.

Figure 7A:
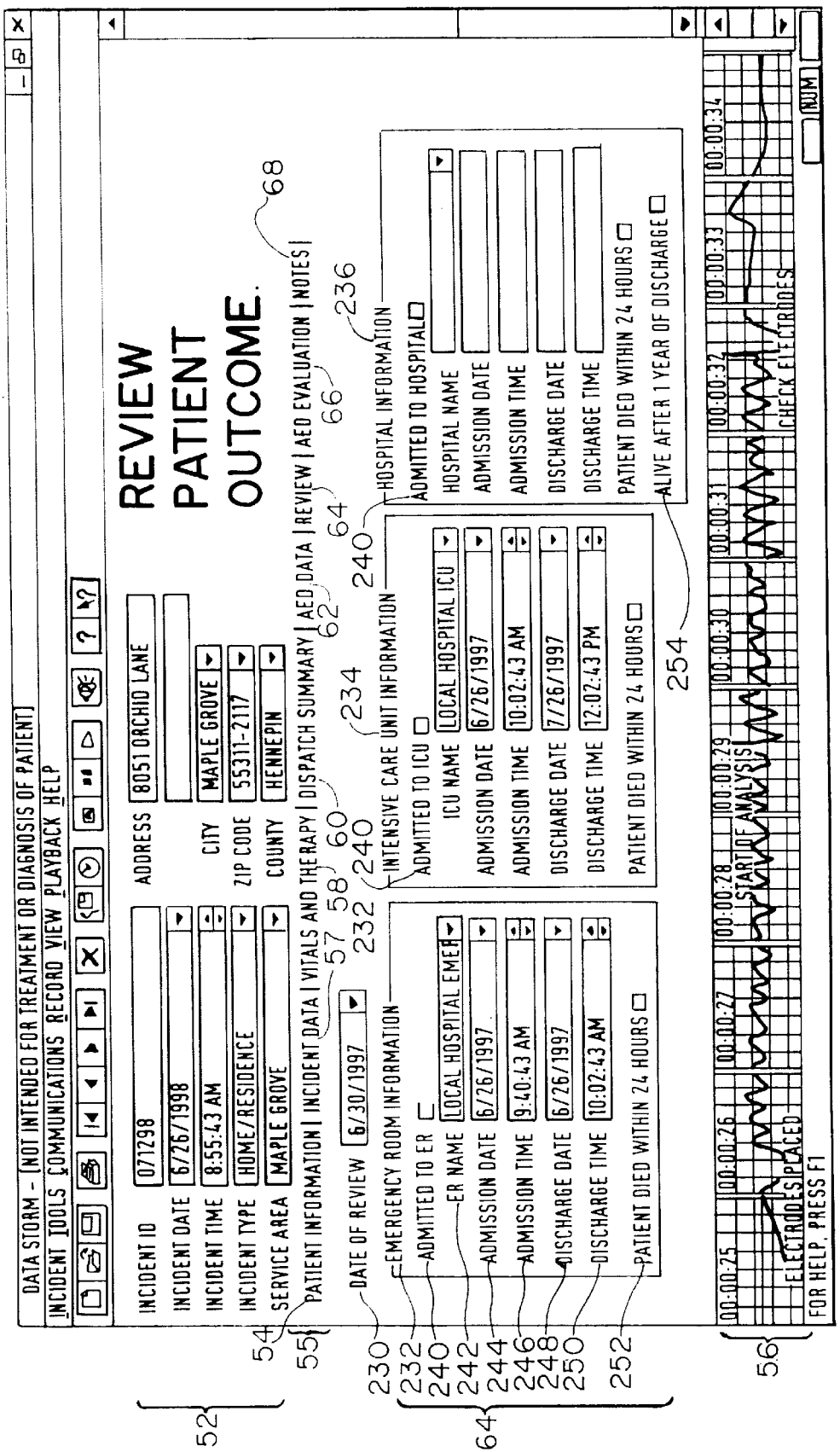
Figure 7B:
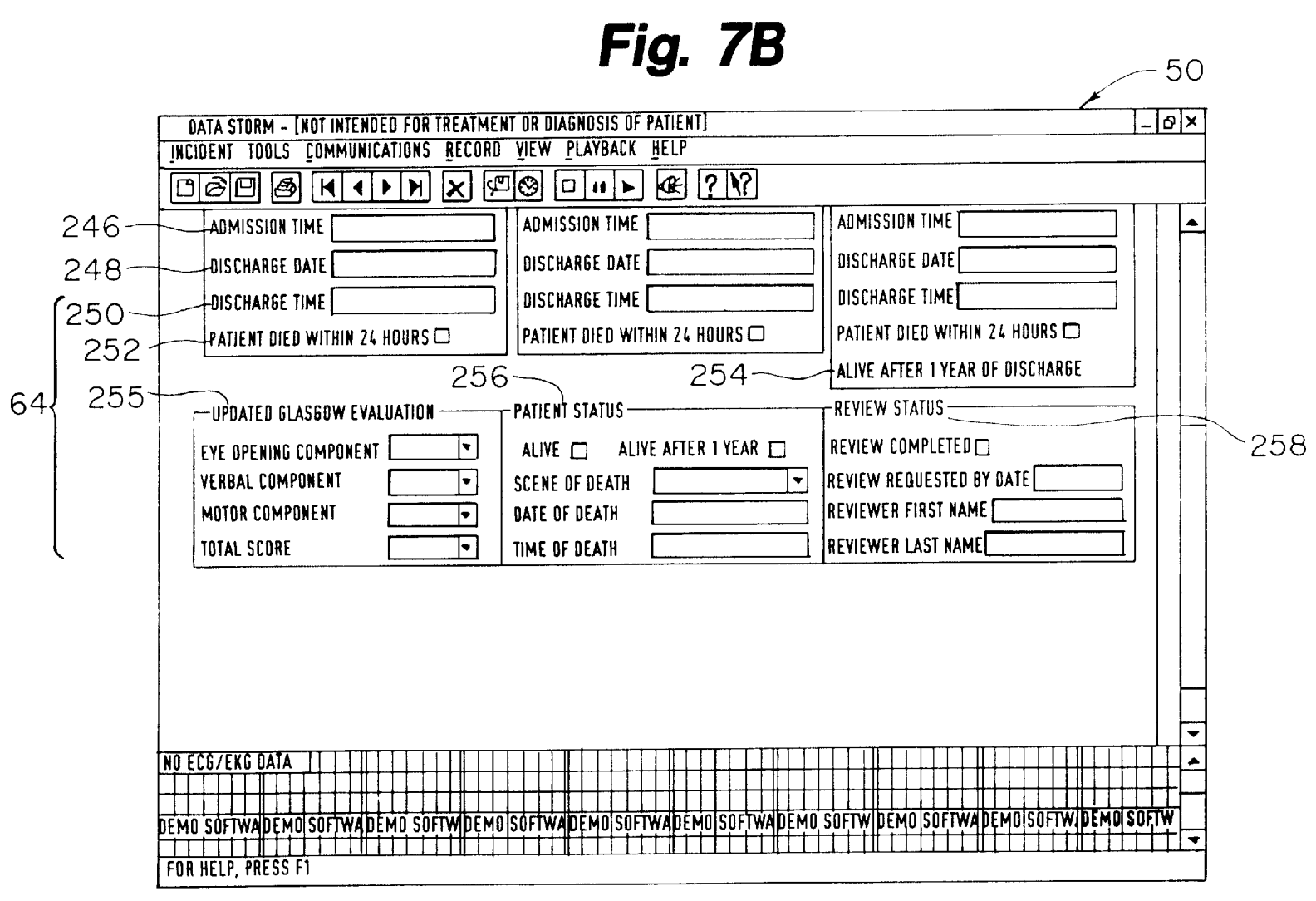

FIG. 7A shows single screen user interface 40 with review tab window 64 selected, which includes the following data fields: date of review 230, emergency room information 232, intensive care unit information 234, hospital information 236. This information is entered into the system by the reviewer away from the cardiac rescue scene. Emergency room information 232, intensive care unit information 234, and hospital information 236 each include the following data fields: admitted to ER (or ICU or hospital) 240, name of ER (or ICU or hospital) 242, admission date 244, admission time 246, discharge date 248, discharge time 250, and patient died within 24 hours 252. Hospital information 236 further includes the data field, alive after one year of discharge 254. FIG. 7B shows a lower portion of review tab window 64, which includes the following additional data fields: updated Glasgow evaluation 255 (including eye opening, verbal, and motor components, with total score), patient status 256 (including alive, alive after first year, scene of death, date of death, and time of death), and review status 258 (including review completed, review due date, reviewer name).

Figure 8:
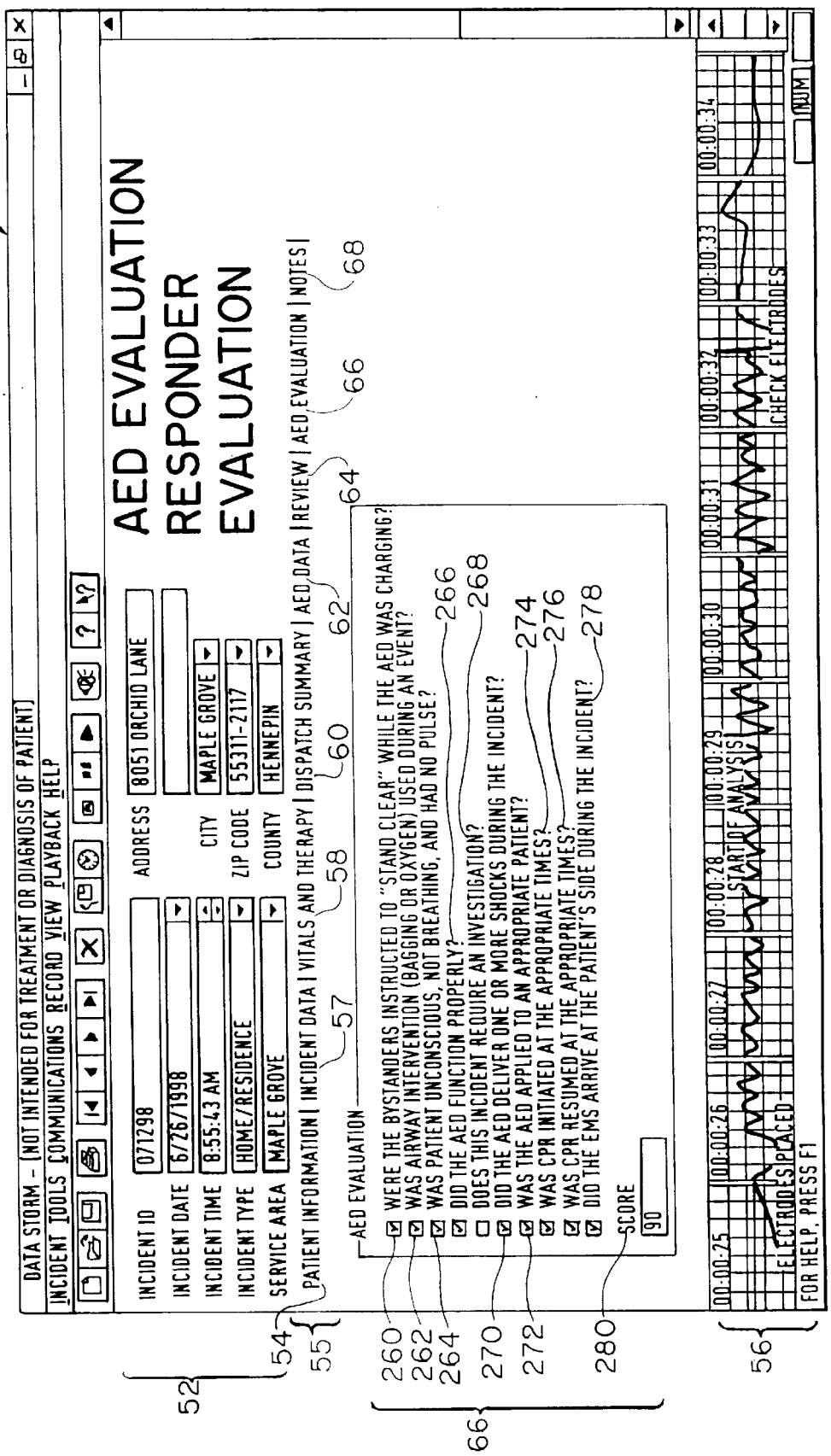
FIG. 8 is a schematic representation of an AED and AED operator review tab window, with optional simultaneous ECG display, of a graphical user interface of the system and method of the present invention.

FIG. 8 shows single screen user interface 40 with AED and responder evaluation tab window 66 selected, and which includes the following data fields: bystanders stand clear instruction 260, airway intervention 262, patient not conscious, not breathing, and no pulse 264, AED function properly 266, incident investigation required 268, AED deliver one or more shocks 270, AED applied to appropriate patient 272, CPR initiated at appropriate time 274, CPR resumed at appropriate times 276, EMS arrive at patient's side during incident 278, and score 280. This evaluation tab window is used for evaluating the AED and AED operator performance.

Figure 9:
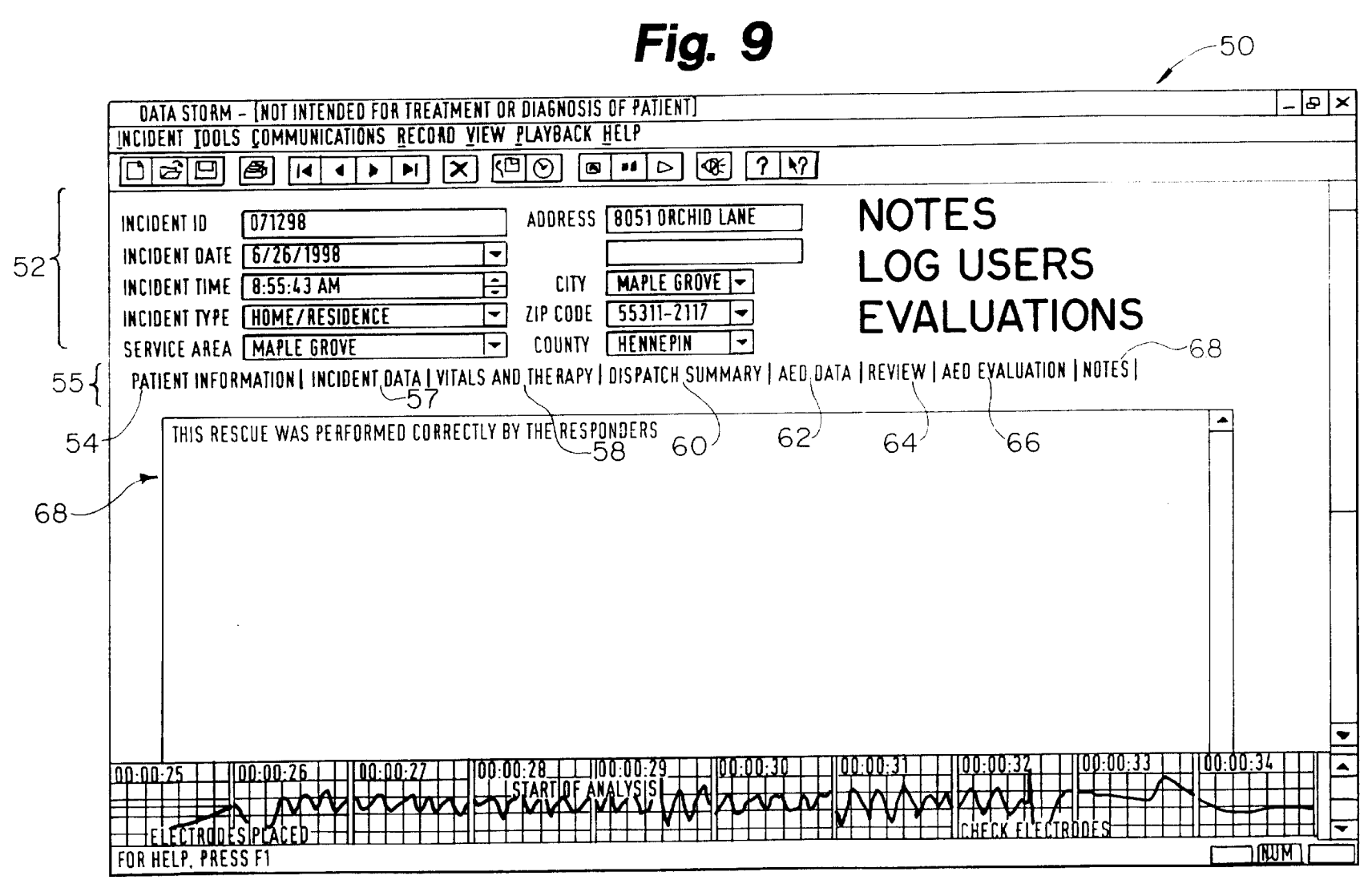

FIG. 9 shows single screen user interface 40 with notes tab window 68 selected. This tab window is for provided for a reviewer to make notes regarding any aspect of the cardiac rescue under review.

Figure 10A:
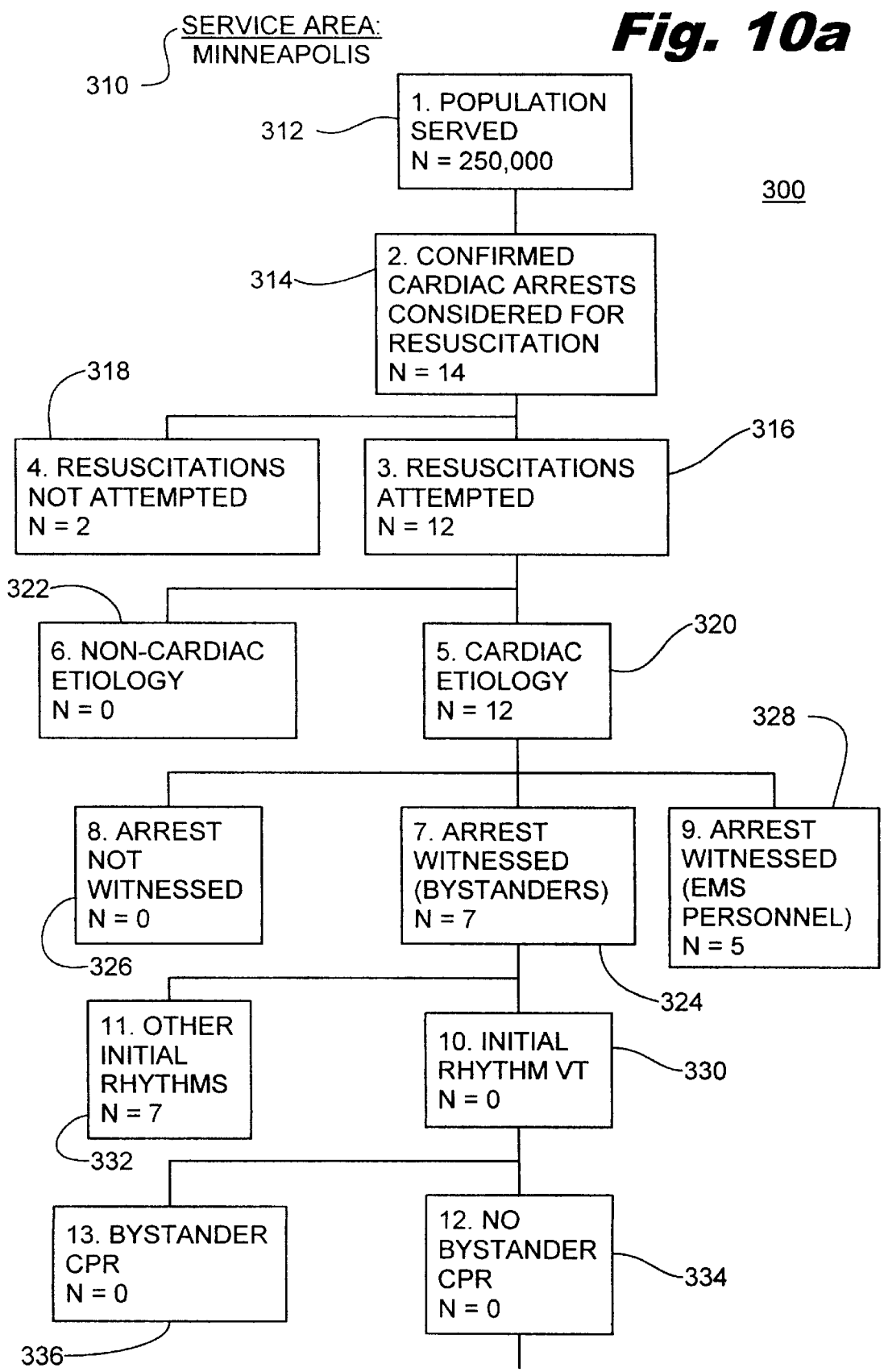
FIG. 10 is a schematic representation of a report of the system and method of the present invention for reporting UTSTEIN data on cardiac arrest incidents.
Figure 10B:
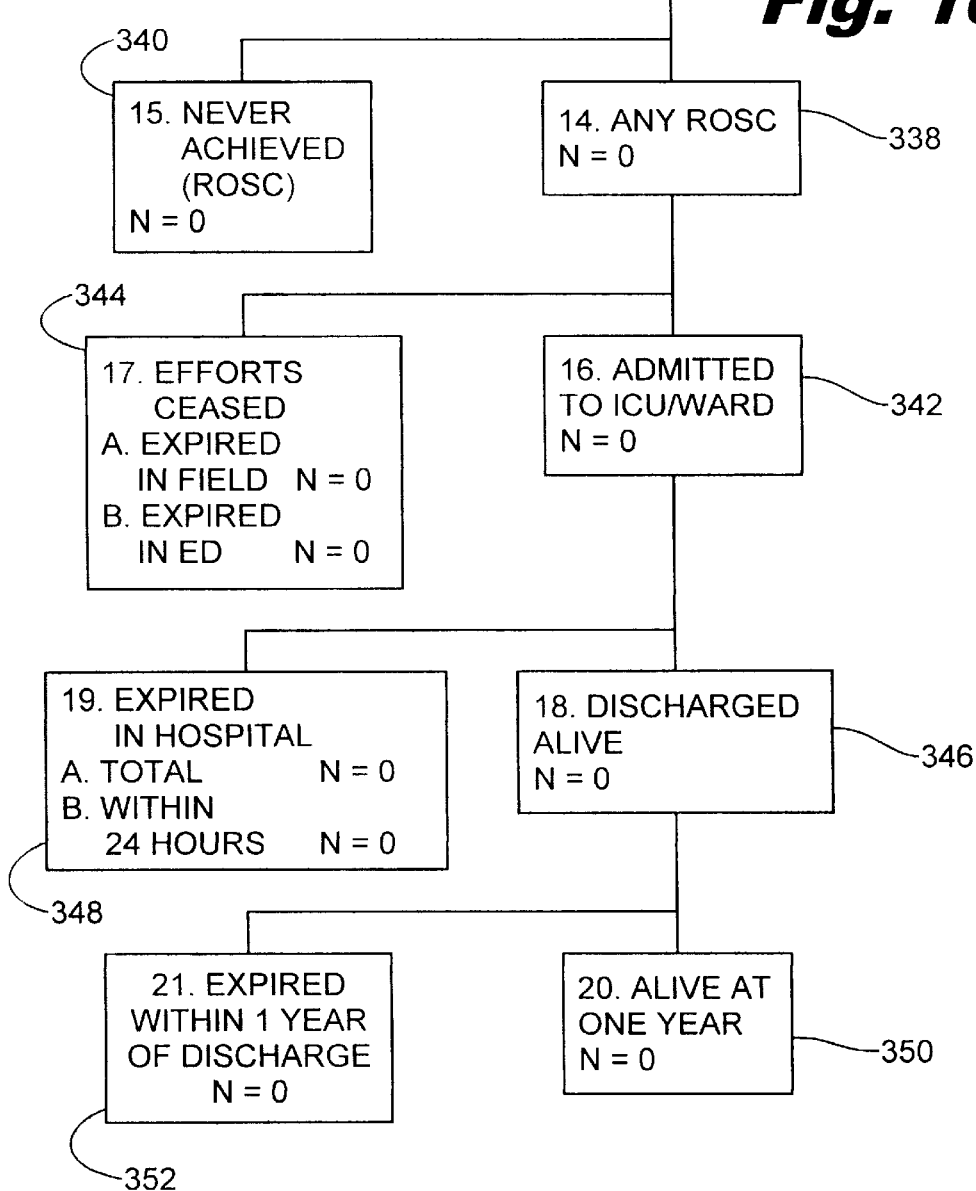

The system and method of the present invention is also capable of generating many types of reports by grouping a selected combination of data fields from one or more tab windows from single screen user interface 40. FIG. 10 shows an UTSTEIN data report 300 on cardiac arrest incidents for ventricular tachycardia with no-bystander CPR. This report follows the Utstein Style Guidelines for Uniform Reporting of Data from Out-of-Hospital Cardiac Arrest. Reports similar to report 300 are available for ventricular tachycardia with bystander CPR, ventricular fibrillation with no-bystander CPR, ventricular fibrillation with bystander CPR, asystole with no-bystander CPR, and asystole with bystander CPR. Each UTSTEIN report includes the following data fields: service area 310, population served 312, confirmed cardiac arrests considered for resuscitation 314, resuscitations attempted 316, resuscitations not attempted 318, cardiac etiology 320, non-cardiac etiology 322, arrest witnessed (bystanders) 324, arrest not witnessed 326, arrest witnessed (EMS personnel) 328, initial rhythm VT 330, other initial rhythms 332, no bystander CPR 334, bystander CPR 336, any resuscitation on spontaneous circulation (ROSC) 338, never achieved (ROSC) 340, admitted to ICU/ward 342, efforts ceased 344 (expired in field or in ED), discharged alive 346, expired in hospital 348 (total or within 24 hours), alive at one year 350, and expired within one year of discharge 352.

Many other reports can be obtained which provide a print out of a selected combination of data fields from one or more tab windows of single screen user interface 40. For example, standard reports include dispatch summary, incident summary, post-market surveillance, ECG summary, and patient follow-up, etc.

In addition to managing the effectiveness of a single or multiple cardiac rescue event, the system and method of the present invention also can be used to track the use and location of AEDs as well as facilitate training of AED operators.

Figure 11:
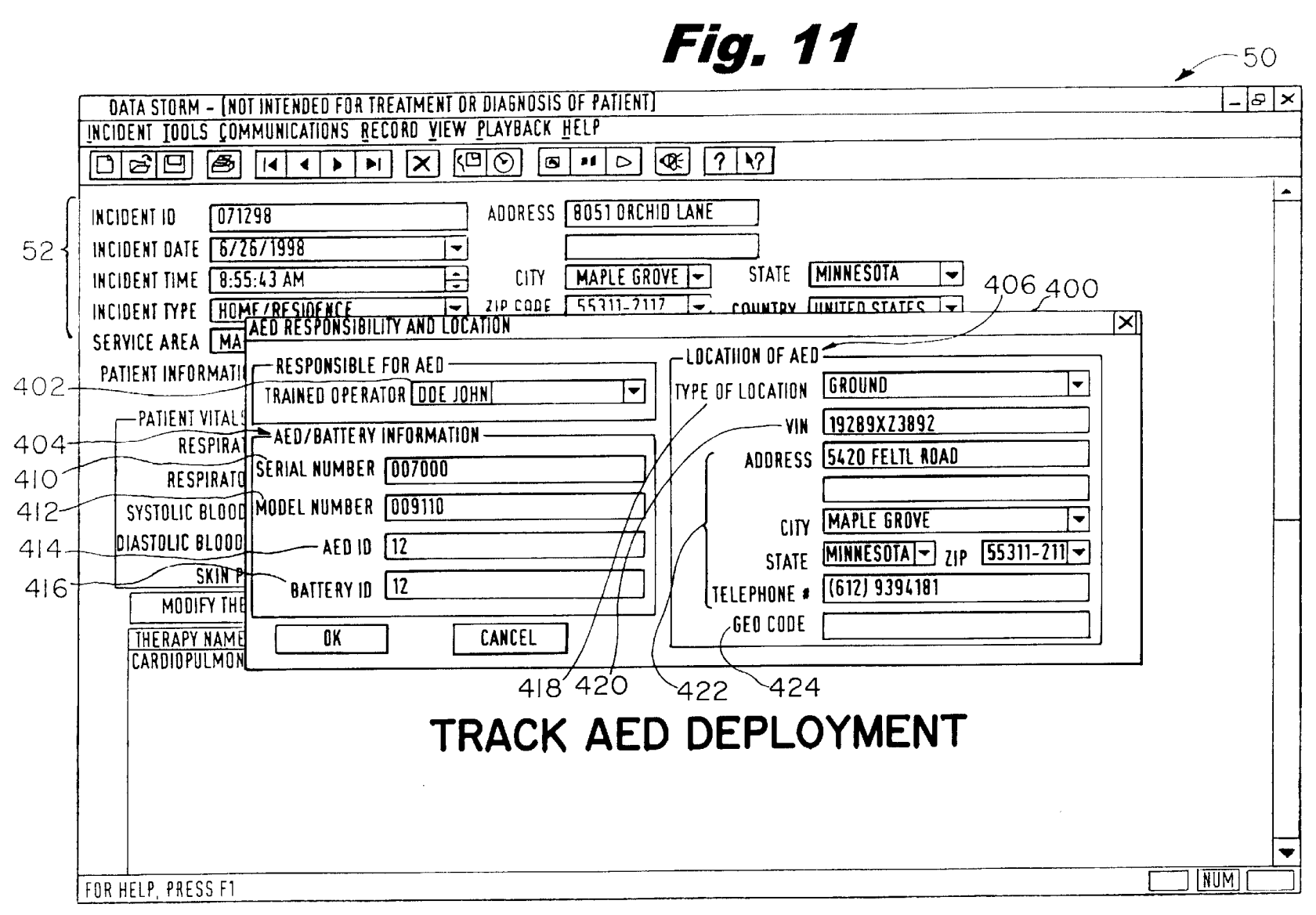

FIG. 11 shows single screen user interface 40 with optional AED deployment tracking tool window 400 selected, which includes the following data fields: AED operator 402, AED/Battery information 404, and AED location 406. AED/battery information 404 further includes serial number 410, model number 412, AED ID 414, and battery ID 416. AED location 406 further includes type of location 418 (e.g., ground), VIN 420, address 422 (street, city, state, zip, telephone), and geographic code 424. Of course, most of this AED data will be loaded into these data fields automatically when the AED data from AED 22 is transmitted from AED 22 into rescue scene computer 26 and then into base computer 34.

Figure 12:
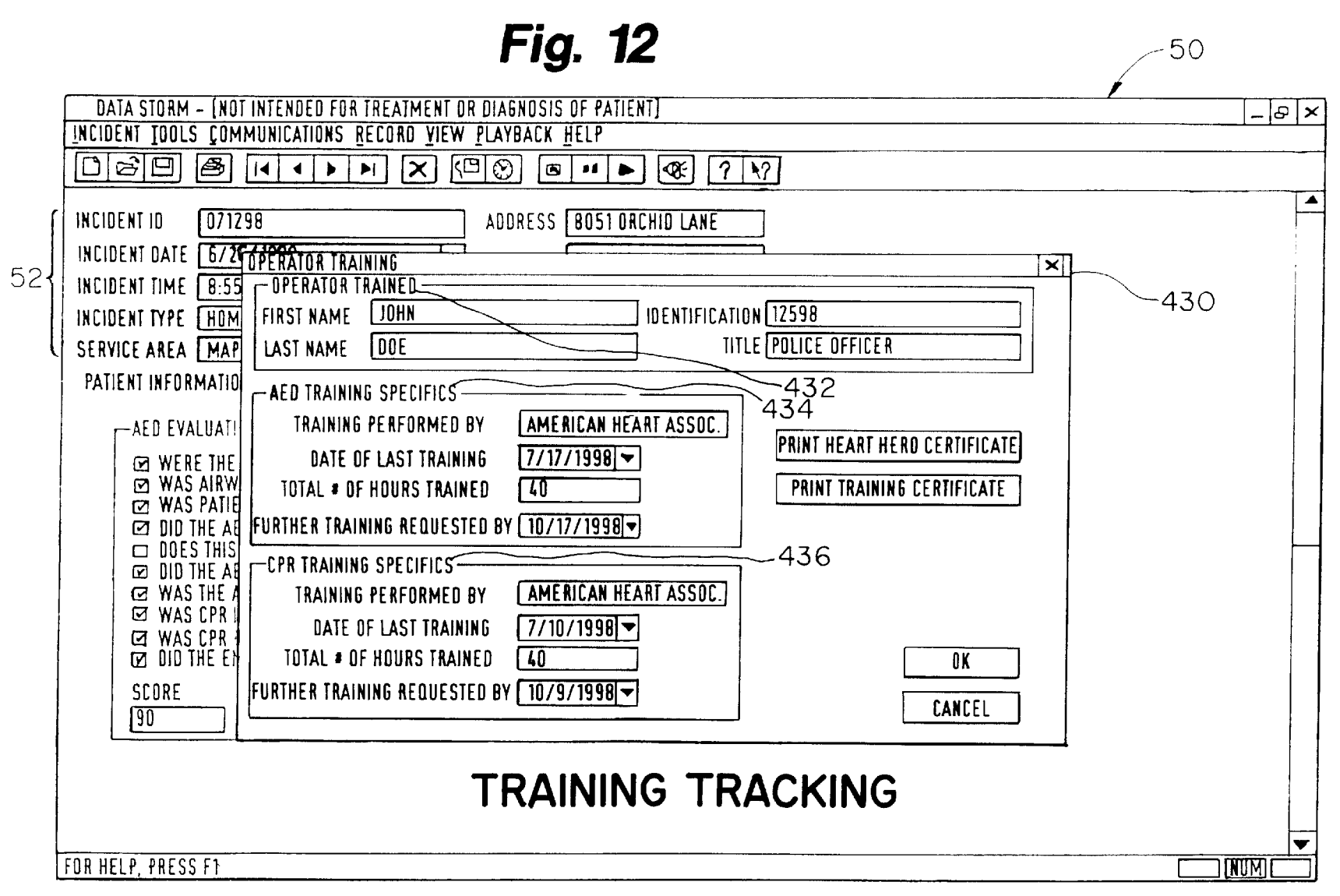

FIG. 12 shows single screen user interface 40 with optional operator training tool window 430 selected, which includes the following data fields: operator trained 432 (name, ID, title) and both AED training specifics 434 and CPR training specifics 436, each including training performed by, date of last training, total number of hours trained, further training by. This data facilitates training of AED operators and tracking of who and how many people are trained AED operators.

The system and method of the present invention have numerous advantageous features. First, a programmed rescue scene computer permits user-observed patient and incident data to be transmitted simultaneously with transmission of ECG data and AED data from the rescue scene to a base computer. This on-scene data collection and simultaneous transmission with the ECG data permits the AED to remain in the field for nearly immediate use in another cardiac rescue event. Second, once the ECG data, AED data, and non-ECG data (patient and incident information, etc.) are in the system, the ECG data is selectively displayed simultaneously with AED data and/or non-ECG patient and incident data on a single screen graphical user interface. This feature greatly facilitates review of the data and ECG since the reviewer need not switch back and forth between a non-ECG data or notes/review screen and the ECC data screen during review. Third, ECG data and AED data imported from the AED, as well as non-ECG data such as patient and incident data, are automatically registered with corresponding predetermined NHSTA codes (or other desired codes) to permit later reporting of the cardiac rescue data in national reporting formats. The NHSTA code registry can be modified on a code-by-code basis and can be selectively deactivated. Fourth, the data fields are based on an Open Database Connectivity (ODBC) format to permit import and export of cardiac rescue data to and from other emergency medical event database management systems, as well as permitting customized reporting by using another ODBC reporting database management software. Together, these features elevate cardiac emergency medical system management to a new level, providing comprehensive and coherent integration of all event and post-event data into a single system. This system and method permits internal or national reporting and rapid assessment and evaluation of the cardiac rescue event. Over time, this system and method will contribute greatly to future benchmarking of cardiac rescue event responses and management, particularly those involving AEDs.

What is claimed is:

1. A method of managing cardiac rescue events comprising the steps of:
   performing a cardiac rescue on a patient at a cardiac rescue site with an automated external defibrillator (AED);
   collecting ECG data at the cardiac rescue event at the cardiac rescue site; and
   collecting automated AED rescue data of the cardiac rescue event at the cardiac rescue site presenting the ECG data and AED rescue data on a screen of a rescue scene computer at the cardiac rescue site.

2. The method of claim 1 and further comprising:
   displaying the ECG data graphically on a display screen simultaneously with the non-ECG rescue data.

3. The method of claim 1 further comprising:
   reviewing the cardiac rescue event by viewing the ECG data on the display screen; and
   inputting analytical observations regarding the cardiac rescue event during the reviewing step.

4. The method of claim 2 further including displaying the ECG data graphically in real time.

5. The method of claim 1 further including the step of displaying the ECG data and AED rescue data in a real time enactment of the cardiac rescue event.

6. The method of claim 1 further comprising:
   collecting AED rescue data including at least one of the following:
   patient information, rescue scene location information, incident and rescue scene assessment information, patient vitals and therapy information, therapy information, rescue dispatch and response information, and AED operator performance information.

7. The method of claim 6 further comprising:
   collecting incident information/rescue scene assessment including chief complaint, cause of injury, provider impression, pre-existing condition, signs and symptoms, injury description, injury intent, incident/patient disposition, safety equipment, factors affecting EMS delivery, suspected drug or alcohol abuse.

8. The method of claim 1 further comprising:
   collecting patient vitals and therapy information including respiratory rate, respiratory effort, blood pressure, skin perfusion and Glasgow information including eye opening, verbal component, motor component, coma score, and therapy including therapy provider, therapy name, and time of therapy.

9. The method of claim 1 further comprising:
   collecting dispatch and response information including at least one of the following: responder facility, vehicle type, dispatch ID and crew members, lights used, sirens used, location of hospital patient transported to, unit dispatched, unit notified, unit responding, arrival at scene, arrival at patient, departure from scene, arrival at destination, and unit back in service.

10. The method of claim 1 further comprising:
    collecting AED rescue data including at least one of the following: an AED serial number, AED model number, AED operator, the real time of and occurrence of the following events: AED lid opening, electrode placement on patient, start of analysis, electrode checking, start of charge, advising operator of shock, delivering shock to patient.

11. The method of claim 1 further comprising:
    collecting AED rescue data including at least one of the following: first defibrillating shock time, initial rhythm, initial rhythm conversion.

12. The method of claim 1 further comprising:
    collecting AED rescue data including at least one of the following: provider type of first CPR, time of first CPR, time CPR discontinued,
    witness type of cardiac arrest, witnessed cardiac arrest, confirmed cardiac arrest, initial cardiac rhythm shocked, return of spontaneous circulation, cardiac etiology, and resuscitation attempted.

13. The method of claim 1 further comprising:
    collecting review data including at least one of the following: review date; admitted to ER, ICU, or hospital; name of ER, ICU, or hospital; admission date; admission time; discharge date; discharge time; patient died within 24 hours; alive after one year of discharge; update Glasgow evaluation including eye opening, verbal, and motor components; patient status including alive, alive after first year, scene of death, date of death, and time of death; and review status including review completed, review due date, reviewer name.

14. The method of claim 13 further comprising:
    establishing a link between a predetermined NHTSA code to a corresponding ECG data or AED rescue data.

15. The method of claim 1 further comprising:
    operably communicatively coupling the AED to the rescue site computer for the automated interchange of certain data therebetween; and
    embedding the predetermined NHSTA code in a background of active data fields to permit selective activation, deactivation, modification, and/or initialization thereof.

16. The method of claim 1 further comprising simultaneously presenting the ECG data and AED rescue on a single screen graphical user interface of the rescue scene computer.

* * * * *

UNITED STATES PATENT AND TRADEMARK OFFICE
CERTIFICATE OF CORRECTION

PATENT NO.    : 6,321,113 B1
DATED         : November 20, 2001
INVENTOR(S)   : William S. Parker, Patrick J. Splinter, Sara M. Lindseth and Matthew G. Bradley It is certified that error appears in the above-identified patent and that said Letters Patent is hereby corrected as shown below:

<u>Title page,</u>
Item [75], Inventors, please change "Sarah Lindseth" to -- Sara Lindseth --.

Signed and Sealed this

Sixth Day of August, 2002

Attest:

Attesting Officer

JAMES E. ROGAN
*Director of the United States Patent and Trademark Office*